(12) United States Patent
Kydar

(10) Patent No.: US 9,733,356 B1
(45) Date of Patent: Aug. 15, 2017

(54) DETECTION OF ANIMATE PRESENCE WITH AN ULTRASONIC SIGNAL

(71) Applicant: SECURE BUBBLE LTD, Kochav Yair (IL)

(72) Inventor: Eytan Kydar, Rehovot (IL)

(73) Assignee: SECURE BUBBLE LTD, Kochav Yair (IL)

(*) Notice: Subject to any disclaimer, the term of this patent is extended or adjusted under 35 U.S.C. 154(b) by 0 days.

(21) Appl. No.: 15/045,269

(22) Filed: Feb. 17, 2016

(51) Int. Cl.
 *G01S 15/52* (2006.01)
 *G08B 21/04* (2006.01)
 *G08B 21/22* (2006.01)
 *G01S 7/539* (2006.01)

(52) U.S. Cl.
 CPC ............ *G01S 15/523* (2013.01); *G01S 7/539* (2013.01); *G08B 21/0423* (2013.01); *G08B 21/22* (2013.01)

(58) Field of Classification Search
 CPC combination set(s) only.
 See application file for complete search history.

(56) References Cited

U.S. PATENT DOCUMENTS

| | | | |
|---|---|---|---|
| 4,197,856 A * | 4/1980 | Northrop | A61B 5/0507 600/453 |
| 4,570,247 A | 2/1986 | Walker et al. | |
| 4,625,199 A | 11/1986 | Pantus | |
| 5,561,641 A | 10/1996 | Nishimori et al. | |
| 5,621,388 A | 4/1997 | Sherburne | |
| 5,638,824 A | 6/1997 | Summers | |
| 5,973,996 A | 10/1999 | Zhevelev et al. | |
| 6,026,340 A | 2/2000 | Corrado et al. | |
| 6,031,482 A | 2/2000 | Lemaitre et al. | |
| 6,248,068 B1 | 6/2001 | Seabron | |
| 6,489,917 B2 | 12/2002 | Geisheimer et al. | |
| 7,045,996 B2 | 5/2006 | Lyon et al. | |
| 7,057,516 B2 | 6/2006 | Donskoy et al. | |
| 7,199,749 B2 | 4/2007 | Greneker, III et al. | |
| 7,417,536 B2 | 8/2008 | Lakshmanan | |
| 7,636,048 B2 | 12/2009 | Krasula et al. | |
| 8,274,386 B1 | 9/2012 | Dea et al. | |

(Continued)

FOREIGN PATENT DOCUMENTS

| | | |
|---|---|---|
| EP | 2010935 | 1/2009 |
| EP | 2215496 | 11/2014 |

(Continued)

OTHER PUBLICATIONS

James M. Sabatier and Alexander E. Ekimov., Ultrasonic Mehods for Human Motion Detection. The University of Mississippi, United States.

(Continued)

*Primary Examiner* — Kabir A Timory
(74) *Attorney, Agent, or Firm* — Soroker Agmon Nordman

(57) ABSTRACT

A system for monitoring animate presence, including one or more ultrasonic transducers configured to transmit an ultrasonic signal, one or more ultrasonic receivers configured to receive an echo signal in response to the transmitted ultrasonic signal, an electronic circuit for comparing the transmitted signal to the received echo signal and identify a phase shift between the signals; wherein the electronic circuit identifies animate presence based on the identified phase shift.

20 Claims, 14 Drawing Sheets

(56) References Cited

U.S. PATENT DOCUMENTS

| | | |
|---|---|---|
| 8,593,279 B2 | 11/2013 | Dreuillet et al. |
| 8,779,966 B2 | 7/2014 | Mohamadi et al. |
| 2002/0120207 A1 | 8/2002 | Hoffman |
| 2004/0015059 A1 | 1/2004 | Friedrichs |
| 2004/0081020 A1 | 4/2004 | Blosser |
| 2007/0135984 A1 | 6/2007 | Breed et al. |
| 2007/0193811 A1 | 8/2007 | Breed et al. |
| 2008/0191871 A1 | 8/2008 | Horak et al. |
| 2008/0292146 A1 | 11/2008 | Breed et al. |
| 2014/0198619 A1 | 7/2014 | Lamb et al. |
| 2014/0299775 A1 | 10/2014 | Kimmel |

FOREIGN PATENT DOCUMENTS

| | | |
|---|---|---|
| WO | 2008001092 | 1/2008 |
| WO | 2014173724 A1 | 10/2014 |

OTHER PUBLICATIONS

Wu Cw, Huang Zy., Using the Phase Change of a Reflected Microwave to Detect a Human Subject behind a Barrier. IEEE Transactions on Biomedical Engineering, vol. 55, No. 1, Jan. 2008.

Wi-Fi Signal Used to Track Moving Humans—even Behind Walls, Jul. 3, 2013.

Mater, O.B., et al., Non Contact Measurement of Vibration Using Airborne Ultrasound, May 1998, Ultrasonics, Ferroelectrics, and Frequency Control, IEEE Transactions, vol. 45 Issue 3, pp. 626-633.

Gueuning, F.E., et al., (1997) Accurate Distance Measurement by an Autonomous Ultrasonic System Combining Time-Of-Flight and Phase-Shift Methods, IEEE Trans. On Instr. and Meas. vol. 46, No. 6, pp. 1236-1240.

* cited by examiner

DETECTION OF ANIMATE PRESENCE WITH AN ULTRASONIC SIGNAL

TECHNICAL FIELD

The present invention relates to automatic detection and/or monitoring of animate presence using an ultrasonic system.

BACKGROUND

Ultrasonic transducers are sensors that convert ultrasound waves to electrical signals and electrical signals to ultrasound waves. Ultrasonic transducers that both transmit and receive are sometimes referred to as ultrasonic transceivers. Ultrasonic transducers are commonly used like radar and sonar systems to detect a target based on the response to a transmitted ultrasonic signal, for example by comparing the time interval between sending the signal and receiving an echo to determine the distance to an object or if it is in motion. Ultrasonic transducers are commonly used in cars as parking sensors to help direct the driver in reversing into a parking space.

In many cases it is of interest to keep track of living people or animals, for example to make sure that they are confined to a specific area or that they are alone in the area. Additionally it may be of interest to verify that they are alive.

In contrast in some cases it may be of interest to negate animate presence, for example to make sure that people or animals do not enter a specific area (e.g. a room) or do not come near a specific object, animal or person. Generally these objectives can be achieved by placing a guard or caretaker to watch the person, animal or object. However it would be desirable to automate this task, to reduce the need to invest in manpower.

An ultrasonic transducer could be used to detect the presence of a person, for example based on motion. However such systems do not differentiate between animate objects and inanimate objects.

SUMMARY

An aspect of an embodiment of the disclosure relates to a system and method of detecting and/or monitoring animate presence in the vicinity of the system. The system includes one or more ultrasonic transducers, receivers and an electronic circuit to analyze the measurements. The electronic circuit analyzes the signals transmitted by the transducers relative to the echo signals received by the receivers in response to identify a phase shift between the signals, the phase shifts provides indication of animate presence, for example a live person or live animal. The system provides notification to a user based on the results of the analysis. Optionally, the system differentiates between a single detected live person or animal and multiple people and/or animals. In some embodiments of the disclosure, the system can identify if the animate presence is from a grown up person, child, infant or specific types of animals.

There is thus provided according to an exemplary embodiment of the disclosure, a system for monitoring animate presence, comprising:

One or more ultrasonic transducers configured to transmit an ultrasonic signal;

One or more ultrasonic receivers configured to receive an echo signal in response to the transmitted ultrasonic signal;

An electronic circuit for comparing the transmitted signal to the received echo signal and identify a phase shift between the signals; wherein the electronic circuit identifies animate presence based on the identified phase shift.

In an exemplary embodiment of the disclosure, the electronic circuit is configured to differentiate between a single animate entity and multiple animate entities. Optionally, the electronic circuit is configured to differentiate between people and animals. In an exemplary embodiment of the disclosure, the electronic circuit is configured to send notification if more than one person is detected in a monitored room. Optionally, the electronic circuit is configured to monitor a Wi-Fi connection and provide a notification if the Wi-Fi connection is unavailable and there exists animate presence.

In an exemplary embodiment of the disclosure, the electronic circuit is configured to monitor the respiratory activity of an observed individual and activate an alarm if the respiratory activity ceases or is abnormal. Optionally, the electronic circuit is configured to monitor animate presence in a closed area and activate an alarm if no animate presence is detected or more than one organism is detected. In an exemplary embodiment of the disclosure, the system includes a communication unit for providing results with a wireless electromagnetic signal. Optionally, the system is configured to monitor animate presence in a room and provide the results to a user in a different room. In an exemplary embodiment of the disclosure, the system is shaped as a sphere to monitor in substantially any direction.

There is further provided according to an exemplary embodiment of the disclosure, a method of monitoring animate presence, comprising:

Transmitting an ultrasonic signal with one or more ultrasonic transducers;

receiving an echo signal in response to the transmitted ultrasonic signal by one or more ultrasonic receivers;

Comparing the transmitted signal to the received echo signal using an electronic circuit to identify a phase shift between the signals; and Identifying animate presence based on the identified phase shift.

In an exemplary embodiment of the disclosure, the electronic circuit is configured to differentiate between a single animate entity and multiple animate entities. Optionally, the electronic circuit is configured to differentiate between people and animals. In an exemplary embodiment of the disclosure, the electronic circuit is configured to send notification if more than one person is detected in a monitored room. In an exemplary embodiment of the disclosure, the electronic circuit is configured to monitor a Wi-Fi connection and provide a notification if the Wi-Fi connection is unavailable and there exists animate presence. Optionally, the electronic circuit is configured to monitor the respiratory activity of an observed individual and activate an alarm if the respiratory activity ceases or is abnormal. In an exemplary embodiment of the disclosure, the electronic circuit is configured to monitor animate presence in a closed area and activate an alarm if no animate presence is detected or more than one organism is detected. Optionally, results of the identifying are provided by an electromagnetic signal. In an exemplary embodiment of the disclosure, the monitoring is performed in a room and results are provided to a user in a different room. In an exemplary embodiment of the disclosure, the system is shaped as a sphere to monitor in substantially any direction.

BRIEF DESCRIPTION OF THE DRAWINGS

The present disclosure will be understood and better appreciated from the following detailed description taken in conjunction with the drawings. Identical structures, elements or parts, which appear in more than one figure, are generally labeled with the same or similar number in all the figures in which they appear. It should be noted that the elements or parts in the figures are not necessarily shown to scale, each element or part may be larger or smaller than actually shown.

DETAILED DESCRIPTION

Figure 1:
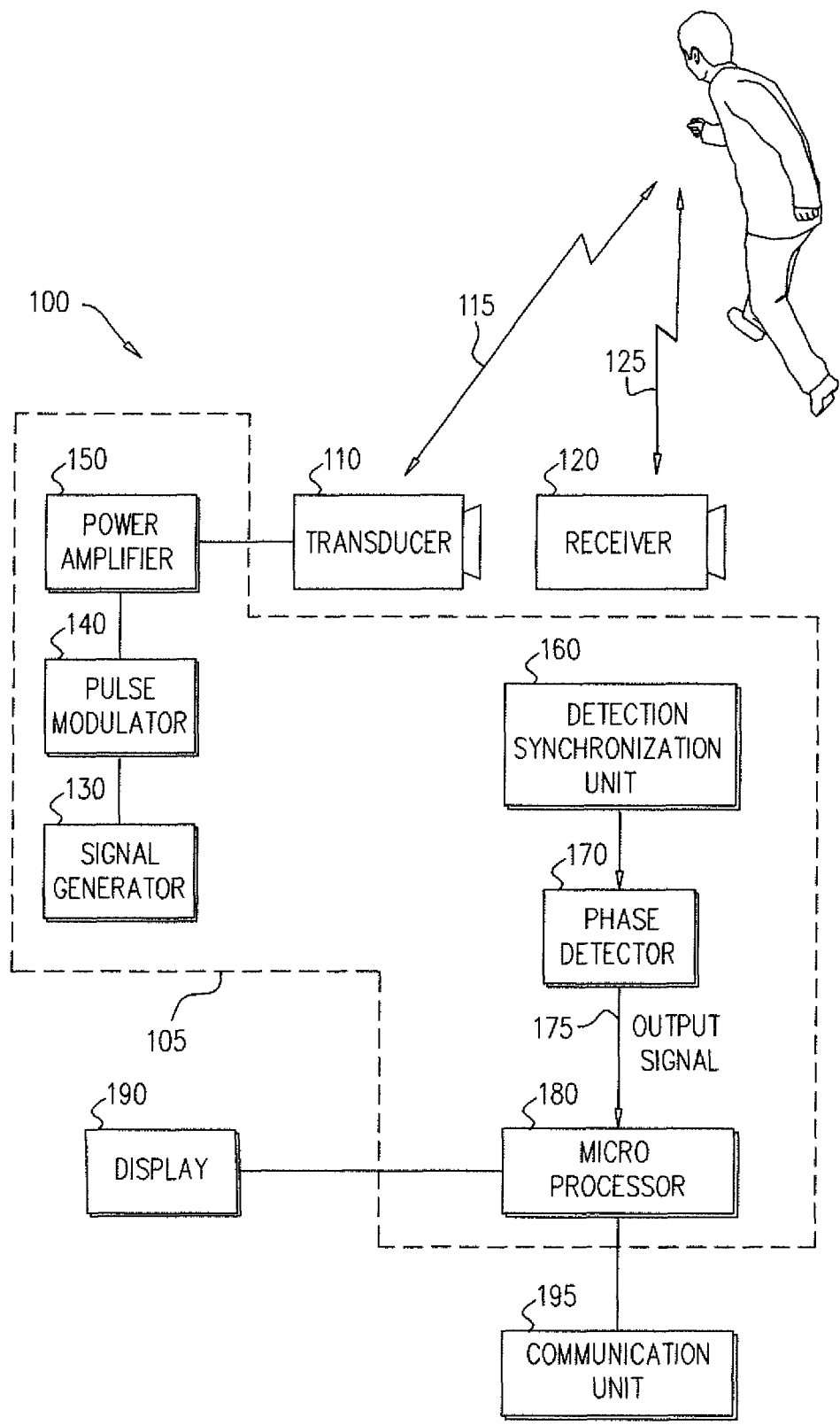
FIG. 1 is a schematic illustration of a system for detecting animate presence, according to an exemplary embodiment of the disclosure.

FIG. 1 is a schematic illustration of a system 100 for detecting animate presence, according to an exemplary embodiment of the disclosure. In an exemplary embodiment of the disclosure, system 100 uses one or more ultrasonic transducers 110 and one or more ultrasonic receivers 120 to monitor activity in the vicinity of the system 100. System 100 transmits a sound wave signal 115 having a frequency in the range of 18 KHz to 1 GHz to enable a reasonable detection range (higher frequencies have a lower detection range). In an exemplary embodiment of the disclosure, the transmitted signal comprises a train of pulses having the selected frequency (for example 10 pulses per second). Receiver 120 records an echo signal 125 resulting from the transmitted sound wave signal 115 being reflected off animate and/or inanimate objects, for example a person or wall. The recorded echo signal 125 is compared to the transmitted signal 115 pulse by pulse. Optionally, an echo signal 125 from animate objects will have a phase shift due to the respiratory system of the person or animal in contrast to the echo signal 125 from inanimate objects that will maintain its phase, for example adult breathing can cause a phase shift having a frequency of about 0.3 Hz and an infant can cause a phase shift having a frequency of about 0.1 Hz. Likewise the heartbeat of an adult can cause a phase shift having a frequency of about 1.2 Hz and an infant can cause a phase shift having a frequency of about 2 Hz. Accordingly by measuring the signal propagation time, signal amplitude and phase shift one can determine the distance to an object and if it is animate or inanimate. Optionally, system 100 is pre-programmed with an empirical list of phase shift ranges for people of different ages (e.g. infants, children and grown-ups) and/or different types and ages of animals (e.g. horses, dogs, cats, bears, tigers, lions, donkeys and other animals). The empirical list is formed by measuring the phase shift resulting from sound wave signal 115 propagating through air (with a velocity of about 300 meters per second) toward various live targets at different distances (e.g. 1-10 meters). In an exemplary embodiment of the disclosure, system 100 can differentiate between people and animals and different type of animals and/or different ages/groups. Optionally, system 100 can differentiate between a single person and multiple people, for example between 2 people and 3 people, or more people.

In an exemplary embodiment of the disclosure, system 100 includes an electronic circuit 105 coupled to the transducers 110 and/or receivers 120, the electronic circuit including one or more of the following units:

1. A signal generator 130 to produce a continuous wave signal with a desired frequency (e.g. between 20-200 KHz). Optionally, the wave form is a sine wave or square wave or other form of wave.

2. A pulse modulator 140 that receives the signal from the signal generator 130 and modulates it to form a train of pulses, for example about 10 pulses a second having the desired frequency. Optionally, each pulse is selected to have a duration of about 1 millisecond thus providing a detection discrimination resolution of about 15 cm.

3. A power amplifier 150 that receives pulses from modulator 140 and amplifies them for transmission with transducers 110.

4. A detection synchronization unit 160 that is gated with the pulse modulator 140 to synchronize the pulses of the received echo signal 125 with the pulses of the transmitted signal 115.

5. A phase detector 170 that receives the echo signal 125 from the receiver 120 and provides an output signal 175 representing the phase shift identified between the echo signal 125 and the wave signal provided by the pulse generator 130.

6. A microprocessor 180 that receives output signal 175 and processes the signal. Optionally, the signal processing removes noise (e.g. FFT, noise reduction) and determines if the phase signal indicates the presence of one or more live people, animal's or inanimate objects.

In an exemplary embodiment of the disclosure, the electronic circuit 105 may include an onboard display 190 or may be connected to an external display e.g. a standard computer display. The display will provide indications to a user regarding the findings of system 100. Alternatively or additionally, electronic circuit 105 is connected to a communication unit 195, for example a Wi-Fi connector, Blue- Tooth connector, Cellular Mobile transmitter, wired link, RF transmitter, an audible alarm or audio-visual alarm to communicate with other computers, networks and/or people. Optionally, the communication unit 195 is used to notify a user, provide an alert or request action.

In an exemplary embodiment of the disclosure, system 100 receives power from a standard domestic power socket (e.g. 110V or 220V). Alternatively or additionally, system 100 may be battery powered so that it is protected against power outage and is independent of a power source at least for a specific duration. Optionally, the battery can be chargeable or replaceable.

Figure 2A:
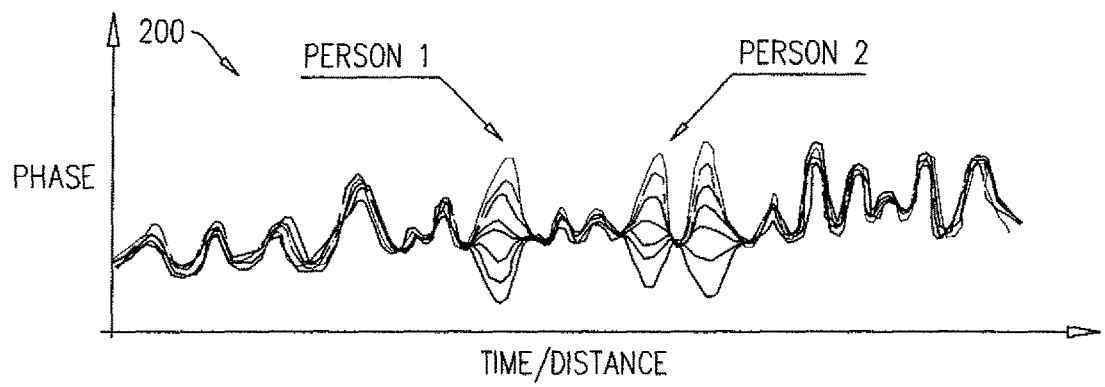
FIG. 2A is a graph of a recorded echo signal in time domain, according to an exemplary embodiment of the disclosure.
Figure 2B:
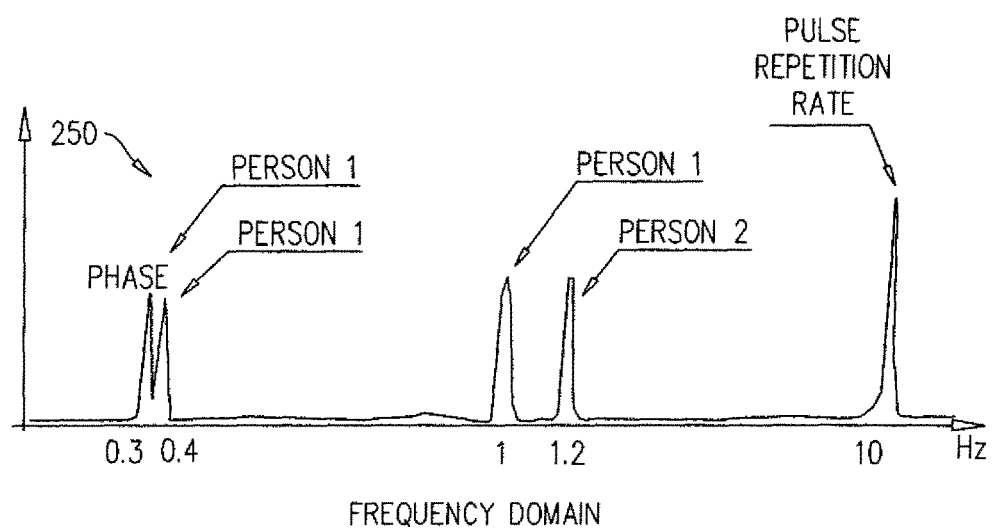
FIG. 2B is a graph of a recorded echo signal in frequency domain, according to an exemplary embodiment of the disclosure.

FIG. 2A is a graph 200 of the recorded echo signal 125 in time domain and FIG. 2B is a graph 250 of the recorded echo signal 125 in frequency domain, according to an exemplary embodiment of the disclosure. Optionally, graph 200 depicts multiple overlapping pulses of the recorded echo signal 125. In most positions the multiple pulses are essentially the same and in specific positions (e.g. affected by animate breathing or heartbeats) the multiple pulses differ. In an exemplary embodiment of the disclosure, the graphs (200, 250) are affected by the presence of two people with distinct heart beats and breathing rates that affect the recorded echo signal 125. Transforming the raw signal as depicted in graph 200 to the frequency domain as depicted in graph 250 helps to enhance detection of the presence of the two people. FIGS. 2A and 2B represent a 10 Hz repetitive pulse with the first person having a breathing rate causing a phase shift of 0.3 Hz and a heartbeat causing a phase shift of 1 Hz. The second person is shown to have a breathing rate causing a phase shift of 0.4 Hz and a heartbeat causing a phase shift of 1.2 Hz.

In an exemplary embodiment of the disclosure, system 100 can be used to monitor a student taking an exam in a room, wherein system 100 is used to ensure that the student works alone (e.g. during a test) without other people in the vicinity. Optionally, system 100 can be set to use a basic signal frequency of about 40 KHz to provide a detection range of about 4 meters.

Figure 3A:
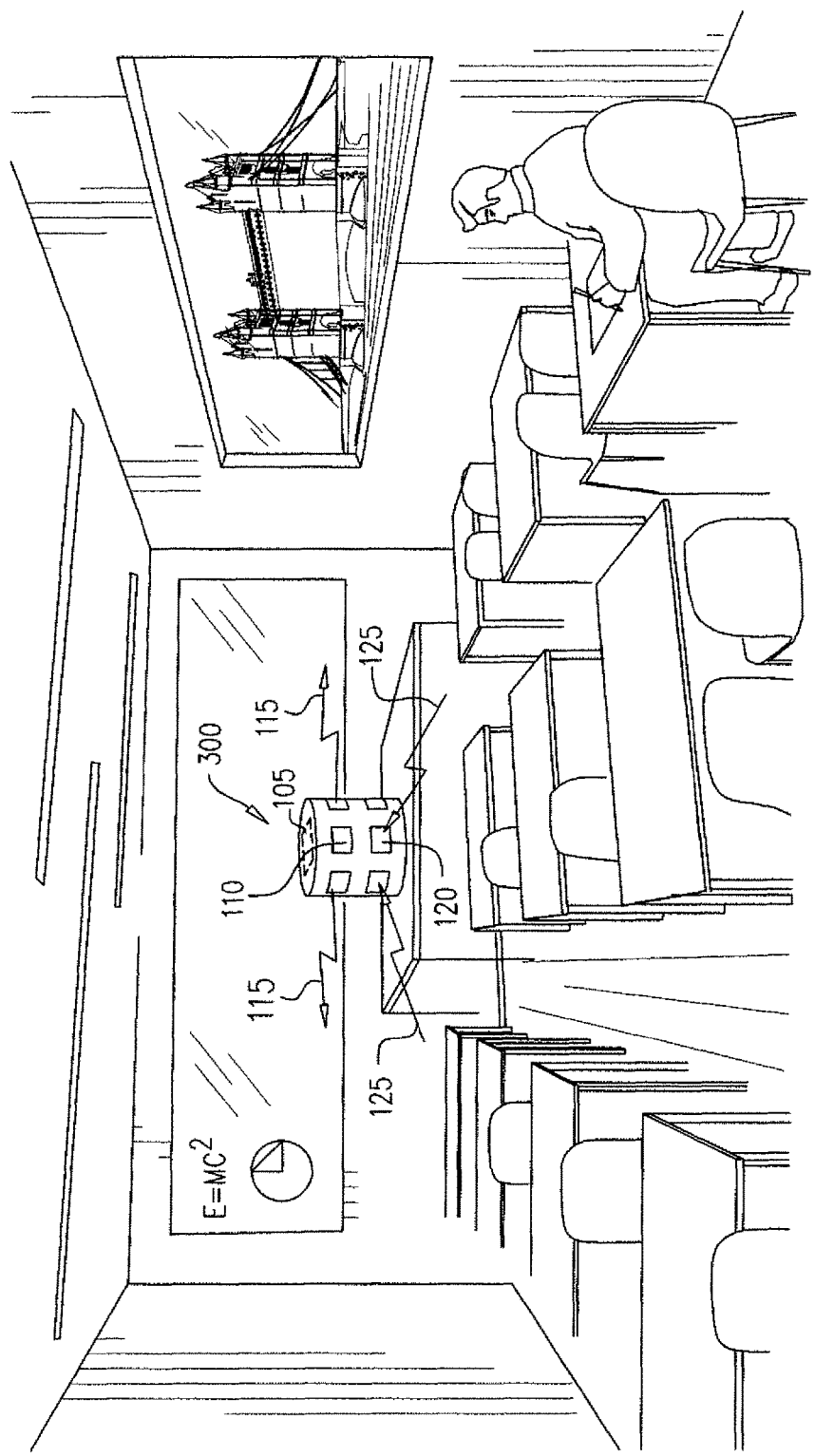
FIG. 3A is a schematic illustration of a system for monitoring animate presence in a room, according to an exemplary embodiment of the disclosure.
Figure 3B:
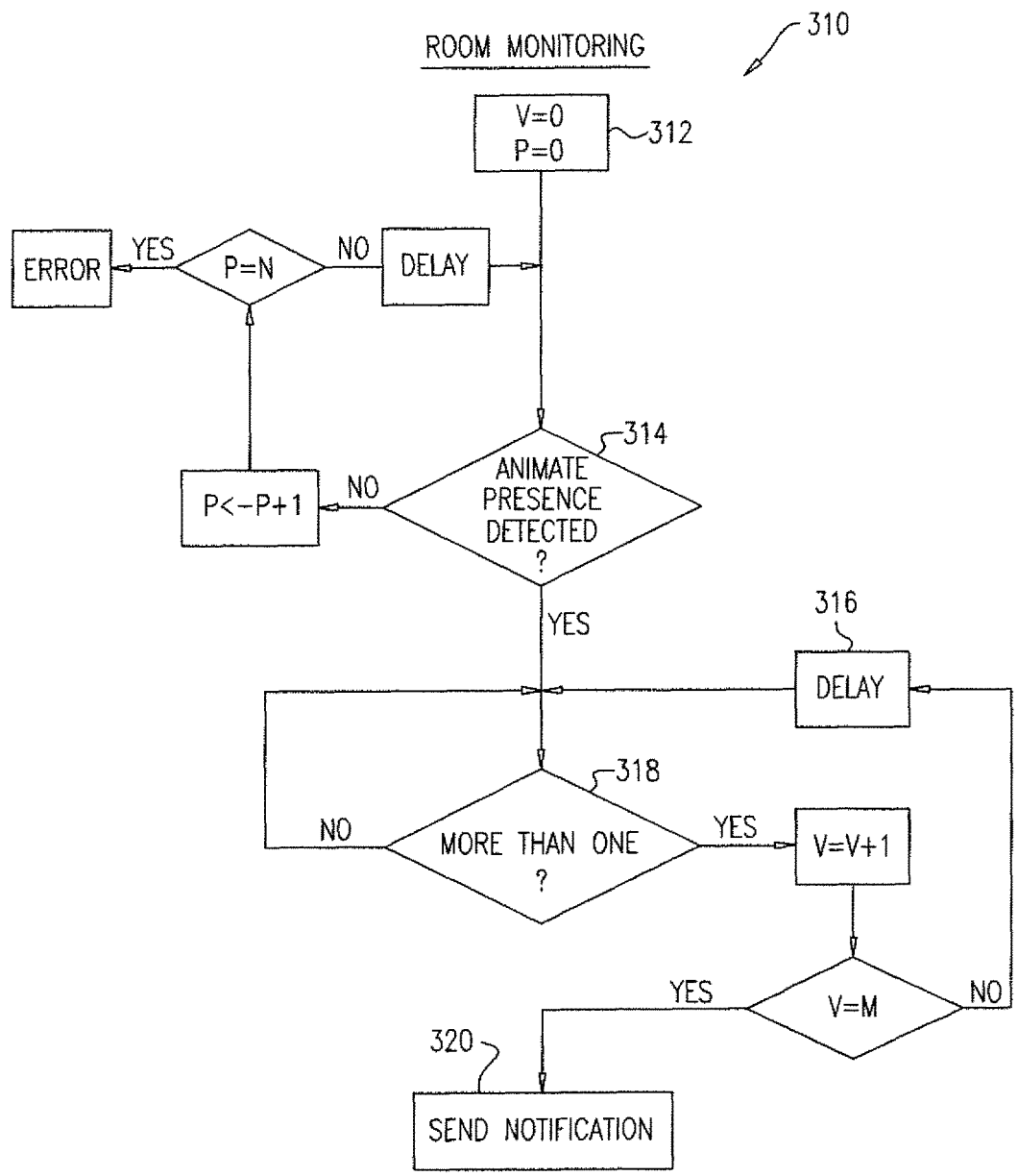
FIG. 3B is a flow diagram of a method of monitoring animate presence in a room, according to an exemplary embodiment of the disclosure.

FIG. 3A is a schematic illustration of a system 300 for monitoring a room for animate presence, and FIG. 3B is a flow diagram 310 of a method of monitoring a room for animate presence, according to an exemplary embodiment of the disclosure. In an exemplary embodiment of the disclosure, system 300 is designed to include electronic circuit 105 with multiple transducers 110 and multiple receivers 120. Optionally, the transducers 110 and receivers 120 are configured to cover 360 degrees around system 300, wherein each transducer may sample for example a meter wide (e.g. up and down) thus essentially sampling a disk shaped area of the entire room surrounding system 300.

In an exemplary embodiment of the disclosure, system 300 is designed to monitor a room and identify if a single person is present or if there are additional people. If the number of people is greater than one an event is recorded and notification may be sent to an administrator. In the flow diagram 310 P denotes the number of attempts to detect animate presence before declaring an error, and V denotes the number of times more than one person can be detected that are allowed to be identified before sending notification to the administrator.

In an exemplary embodiment of the disclosure, P and V are initially set to zero 312. System 300 monitors the room and searches for animate presence 314. Optionally, if no animate presence is detected system 300 keeps waiting or may provide an alert after a time limit defined by P. If animate presence is detected then if more than one person is detected 318 then V is incremented and system 300 continues to check after a preselected time delay 316 if the extra people left the room and only one person remains, for example a person may be allowed to enter the room for a short period to provide test papers to the student. If more than one person is detected again and again, V is incremented and after a pre-selected number of time delays (m) notification is sent 320 to the administrator to take actions.

In an exemplary embodiment of the disclosure, system 300 may be used to monitor a person taking a test at home. Optionally, the person is required to isolate himself in a room and activate system 300 at the beginning of the test. If the presence of other people is detected the test can be invalidated.

Figure 4A:
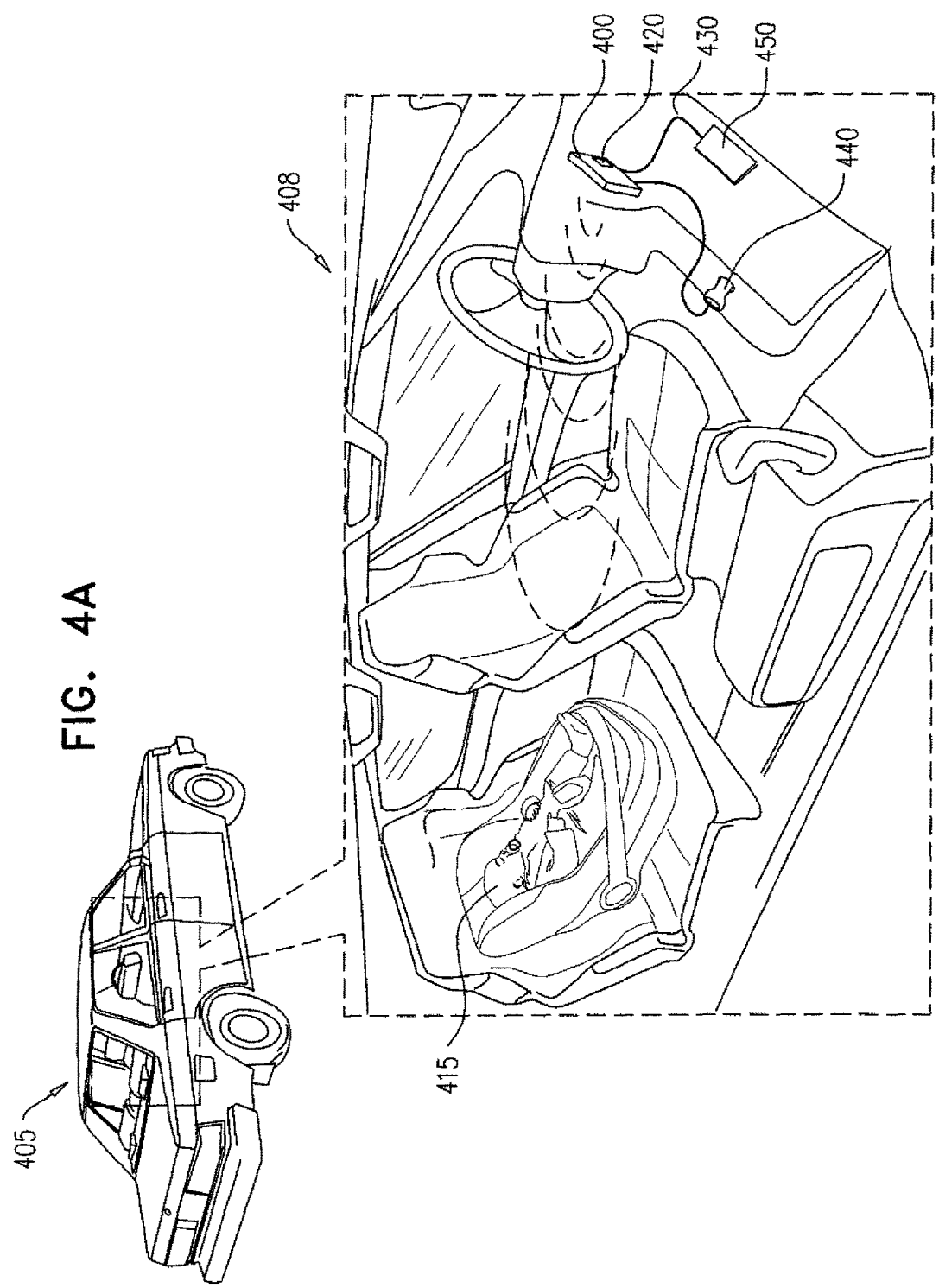
FIG. 4A is a schematic illustration of a system for monitoring animate presence in a vehicle, according to an exemplary embodiment of the disclosure.
Figure 4B:
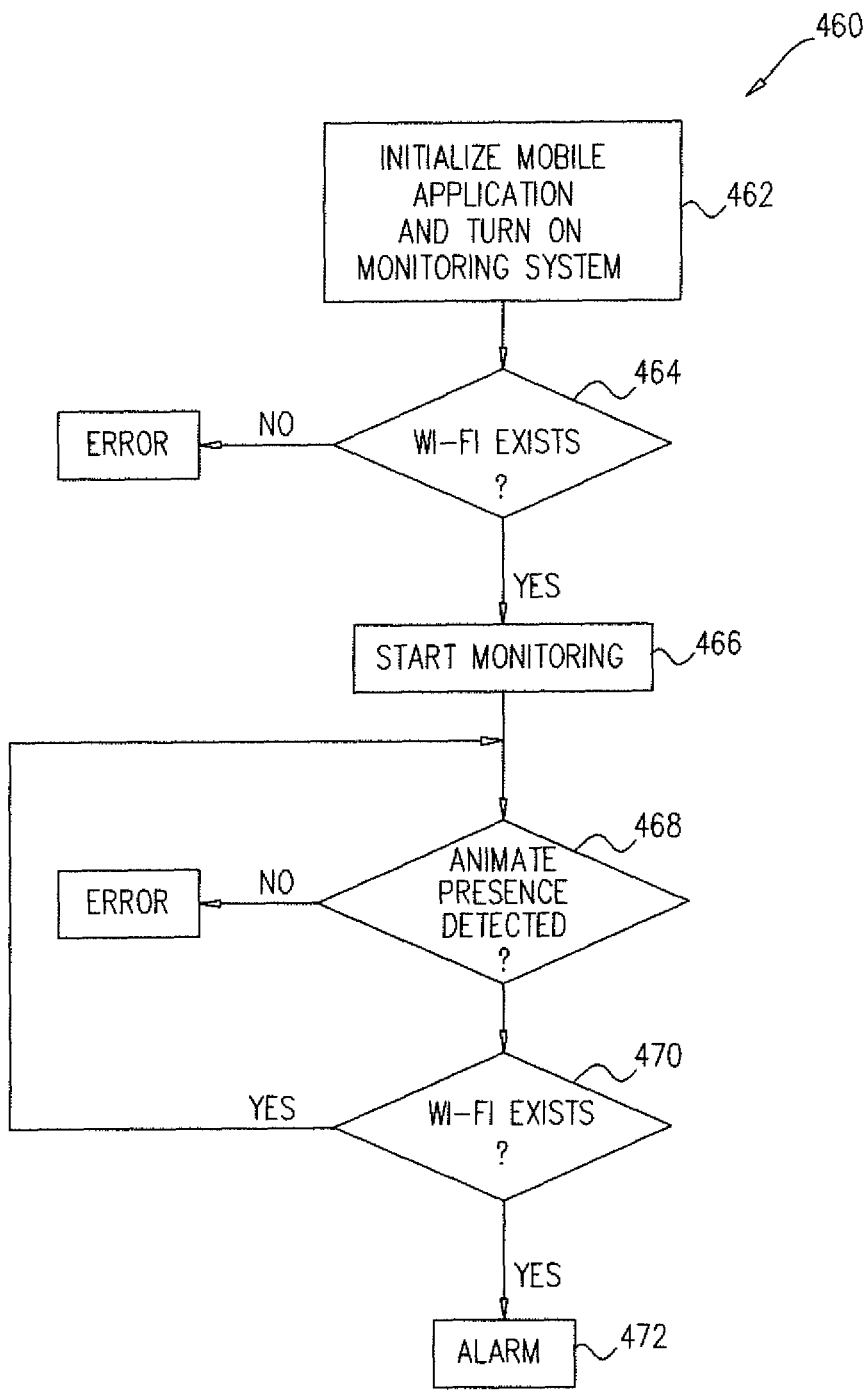
FIG. 4B is a flow diagram of a method of monitoring animate presence in a vehicle, according to an exemplary embodiment of the disclosure.

FIG. 4A is a schematic illustration of a system 400 for monitoring animate presence in a vehicle 405 and FIG. 4B is a flow diagram 460 of a method of monitoring animate presence in the vehicle 405, according to an exemplary embodiment of the disclosure. In an exemplary embodiment of the disclosure, system 400 is installed in vehicle 405, for example by using an attachment means 450 (e.g. a vacuum rubber with a rod) to attach it to a window or roof of the vehicle 405. Optionally, the system 400 includes one or more transducers 110 and receivers 120 to monitor an angle of about 60-90 degrees to detect animate presence in the vehicle 405, for example an infant 415 in the front seat or back seat of the vehicle 405. Alternatively or additionally, in a large vehicle 405 (e.g. a bus or truck) the system 400 may be installed in the center of the vehicle with detection ability of about 180 degrees or even 360 degrees. Optionally, system 400 is powered from the cigarette lighter socket 440 by a cable 430 or directly hardwired to the vehicle electronic system.

In an exemplary embodiment of the disclosure, system 400 supports cellular communications with a sim card 420 in communication unit 195 to notify a pre-programmed telephone in case a determination is made that a monitored person 415 (e.g. infant or handicapped person) is left unattended in the vehicle 405 for more than a pre-selected time. As shown in FIG. 4B the user (e.g. the vehicle driver) initializes a mobile application 462 that provides local Wi-Fi communications to system 400. Additionally, the user turns on system 400. System 400 checks 464 if there exists Wi-Fi communication with the application on the user's mobile device. If yes system 400 starts monitoring 466 the vehicle (e.g. a specific seat or area that system 400 is aimed at). Optionally, system 400 provides notification (e.g. a LED or audio signal) that it has started to monitor, so that if it fails to start the user is notified that an error has occurred and can troubleshoot the system 400, for example check if the application is active on his/her mobile device or check for other errors. In an exemplary embodiment of the disclosure, system 400 initially checks for animate presence 468 for monitoring. If animate presence is detected (e.g. an infant in the monitored area of the vehicle), then system 400 checks for the presence of Wi-Fi communication 470 from the user's mobile device. As long as Wi-Fi communication is available and the animate presence is there system 400 keeps monitoring. However if Wi-Fi communication is lost for a pre-selected time (e.g. because the driver left the vehicle) but animate presence remains then system 400 will activate an alarm 472, for example by calling the user and/or other pre-programed entities (e.g. father, mother, other relatives or calling center) over a cellular network (e.g. using sim card 420) and provide notification that the monitored person 415 is left unattended in the vehicle.

Figure 5A:
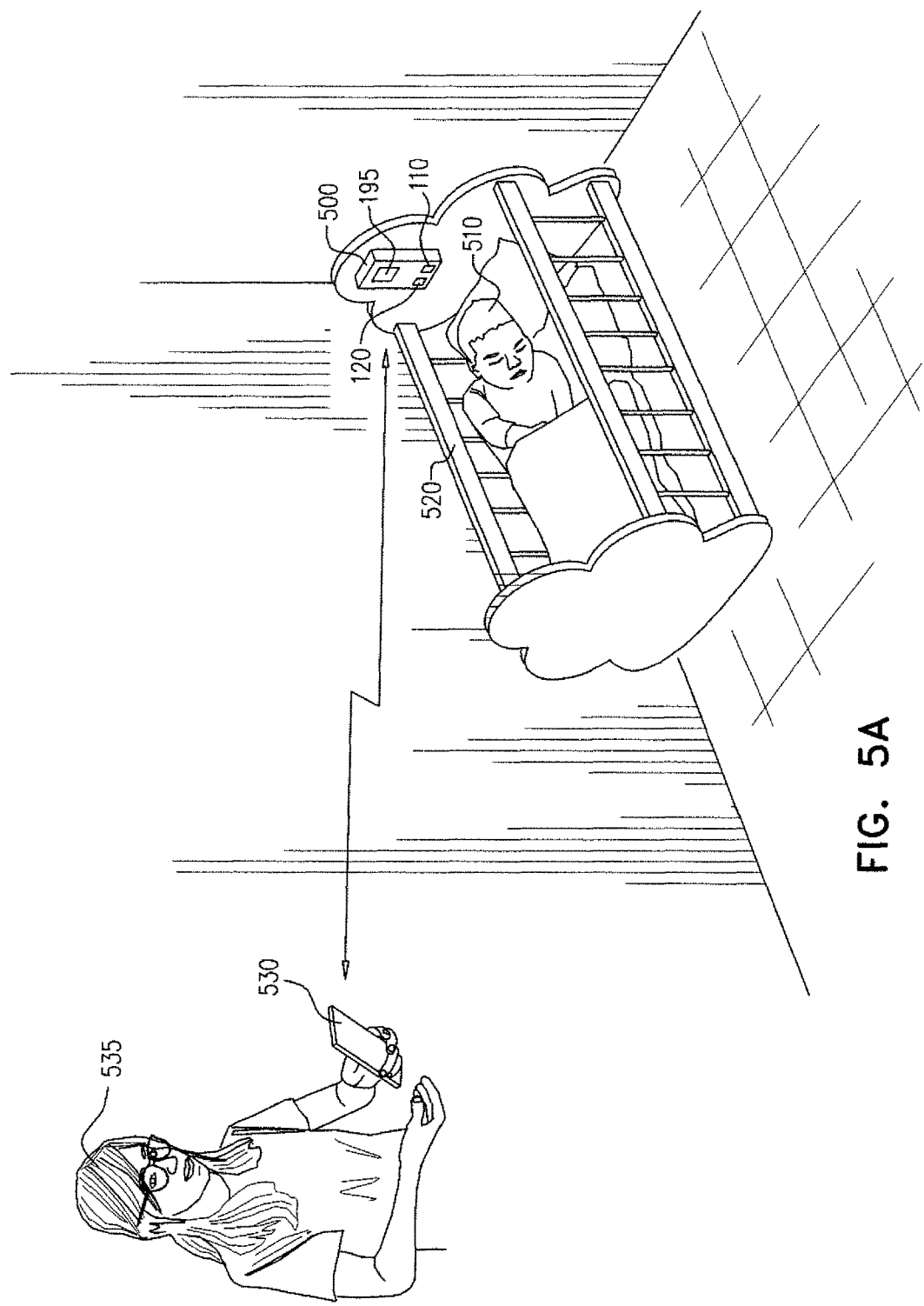
FIG. 5A is a schematic illustration of a system for monitoring respiratory activity of an infant, according to an exemplary embodiment of the disclosure.
Figure 5B:
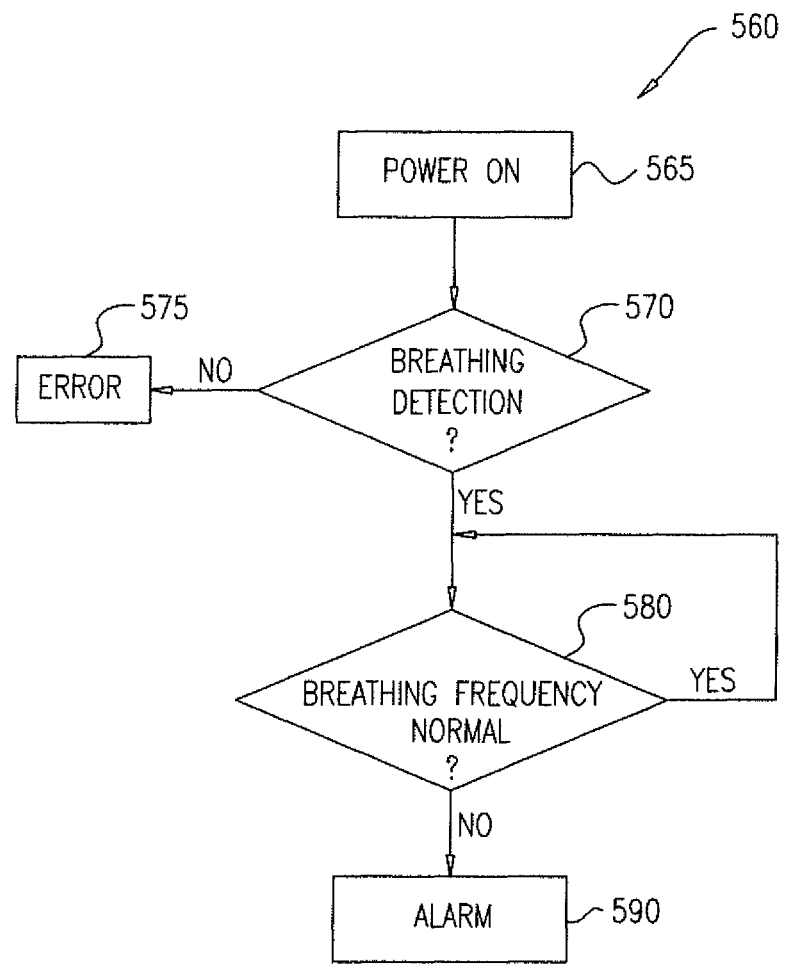
FIG. 5B is a flow diagram of a method of monitoring respiratory activity of an infant, according to an exemplary embodiment of the disclosure.

FIG. 5A is a schematic illustration of a system 500 for monitoring respiratory activity of an infant 510 and FIG. 5B is a flow diagram 560 of a method of monitoring respiratory activity of an infant 510, according to an exemplary embodiment of the disclosure. In an exemplary embodiment of the disclosure, system 500 is placed near the body or face of the infant 510, for example on a side of a crib 520. System 500 is equipped with one or more ultrasonic transducers 110 and one or more ultrasonic receivers 120 that are arranged, for example with a dispersion angle of between 50 to 70 degrees since in general an infant using system 500 does not move much. Optionally, a frequency of about 200 KHz instead of about 40 KHz can be used to improve detection resolution, since the measured distance is small (e.g. about 1 meter).

In an exemplary embodiment of the disclosure, system 500 is powered on 565 after putting the infant 510 in the crib 520. Then system 500 detects breathing 570 of the infant 510. If no breathing is detected an indication of an error 575 is provided by system 500 otherwise system 500 verifies 580 that the breathing is in the normal range for an infant, for example forming a phase shift of less than 0.6 Hz. If the breathing is normal system 500 continues to monitor the infant 510. Otherwise if the breathing ceases or is abnormal system 500 activates an alarm 590 that uses communication unit 195 to communicate with a remote receiver 530 that is located, for example with the mother 535 or father. Optionally, the remote receiver 530 may be communicated by an RF signal or over a Wi-Fi network. In some embodiments of the disclosure, the remote receiver may be a mobile telephone that is contacted by system 500 having a sim card in communication unit 195. In some embodiments of the disclosure, communication unit 195 is connected by a cable to remote receiver 530.

Figure 6A:
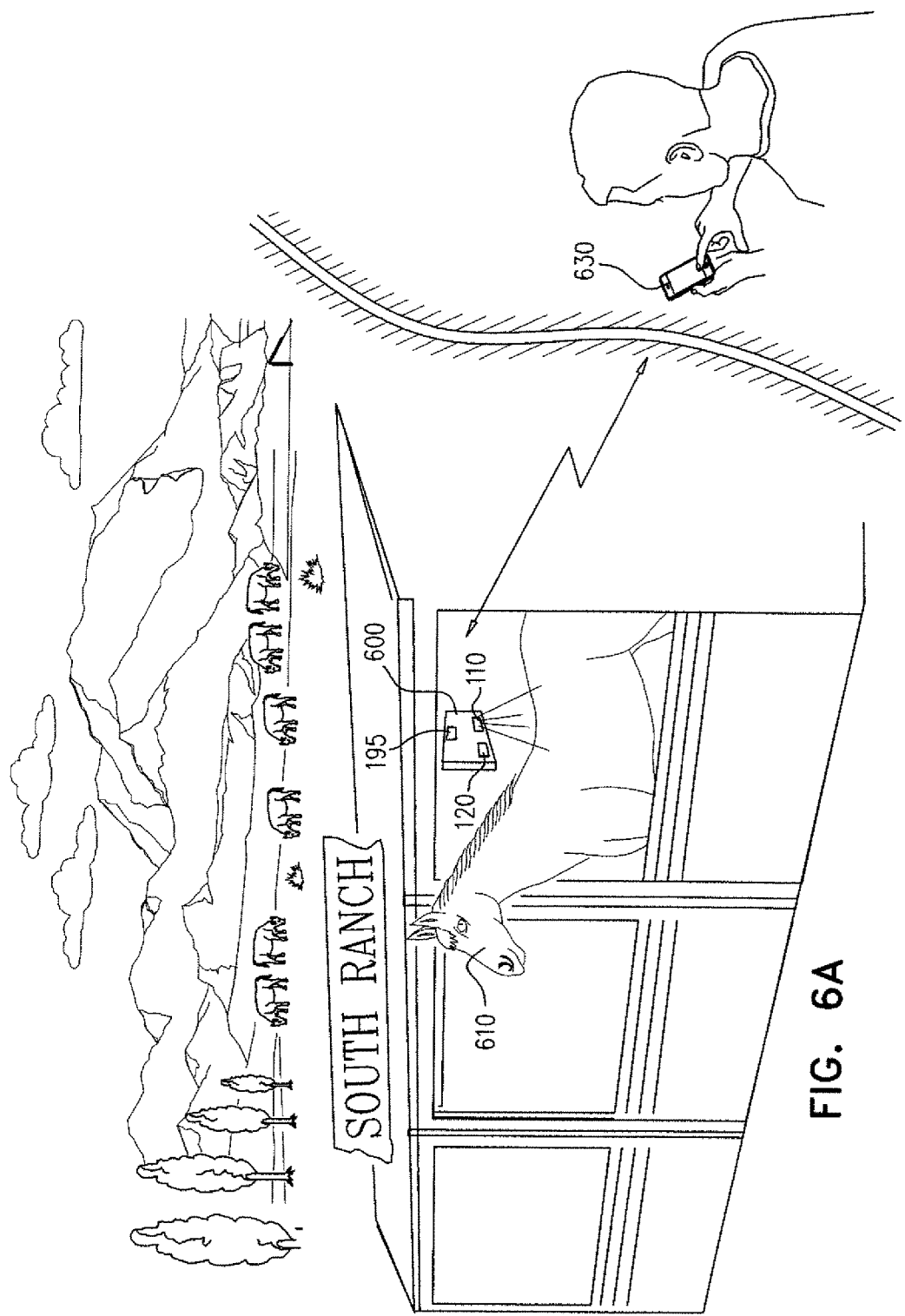
FIG. 6A is a schematic illustration of a system for guarding an animal, according to an exemplary embodiment of the disclosure.
Figure 6B:
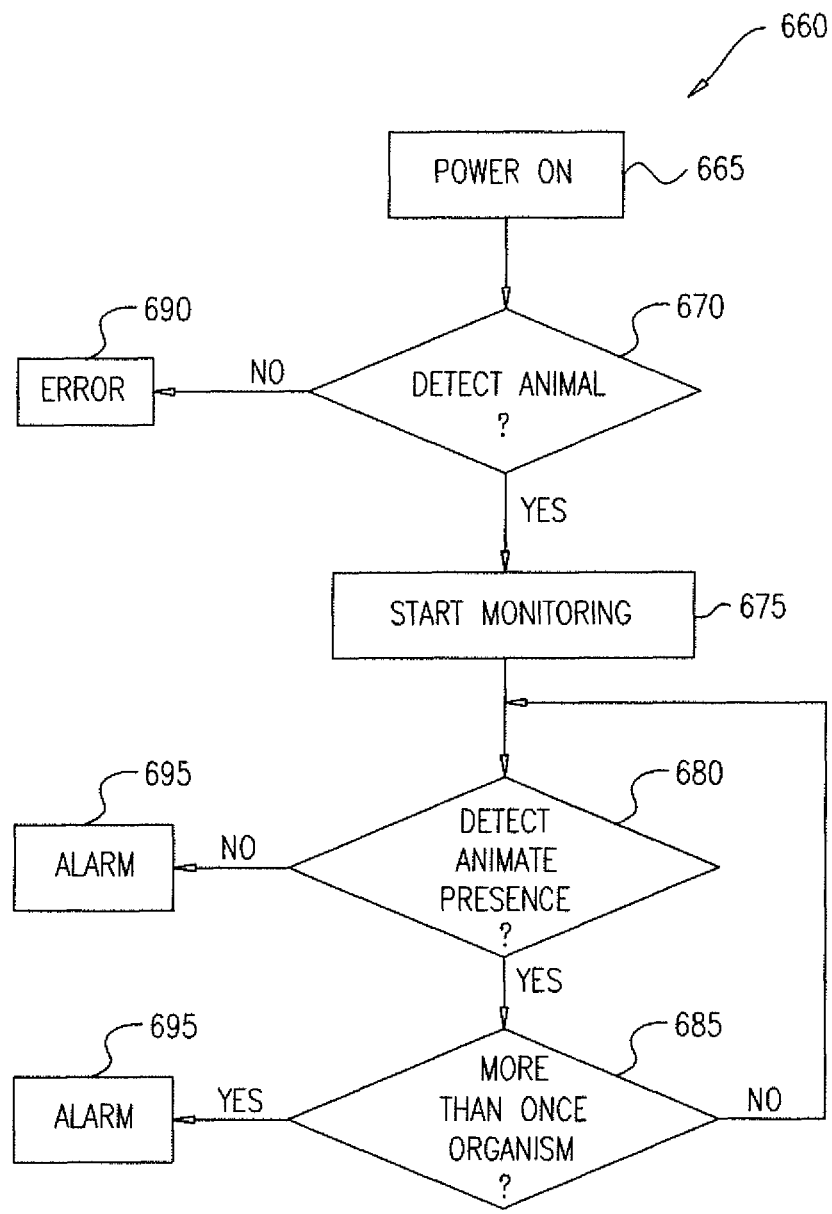
FIG. 6B is a flow diagram of a method of guarding an animal, according to an exemplary embodiment of the disclosure.

FIG. 6A is a schematic illustration of a system 600 for guarding an animal and FIG. 6B is a flow diagram 660 of a method of guarding an animal 610, according to an exemplary embodiment of the disclosure. Some animals are expensive and it desirable to have them monitored to prevent theft, for example purebred horses. In an exemplary embodiment of the disclosure, system 600 monitors the animal and notifies a caretaker if anybody comes near the animal 610 or if another animal is placed near the animal 610. Optionally, system 600 includes one or more ultrasonic transducers 110 and one or more ultrasonic receivers 120. Optionally, the transducers 110 and receivers 120 are arranged to monitor an angle of between 120 to 180 degrees to cover an entire closed area such as a stable or stall.

In an exemplary embodiment of the disclosure, system 600 is powered on 665 and attempts to detect 670 the animal 610. If no animal is detected an error indication 690 will be produced so that the user can fix the error so that system 600 can function properly. If the animal 610 is detected the system 600 starts to monitor 675 the animal 610. Optionally, system 600 continuously detects animate presence 680. If animate presence is not detected an alarm 695 is activated. Optionally, the alarm uses communication unit 195 to notify the caretaker that security has been breached. Communication may be realized in the form of a sim card communicating over a cellular network or by a local Internet connection (e.g. Wi-Fi). Optionally, a vocal message may be transferred or a text message (e.g. SMS or other applications). If animate presence is detected, system 600 checks if more than one organism was detected 685, for example if another animal or person enters the closed area. If only a single organism was detected system 600 continues to monitor the animal 610. Otherwise system 600 activates an alarm to notify the caretaker.

Figure 7A:
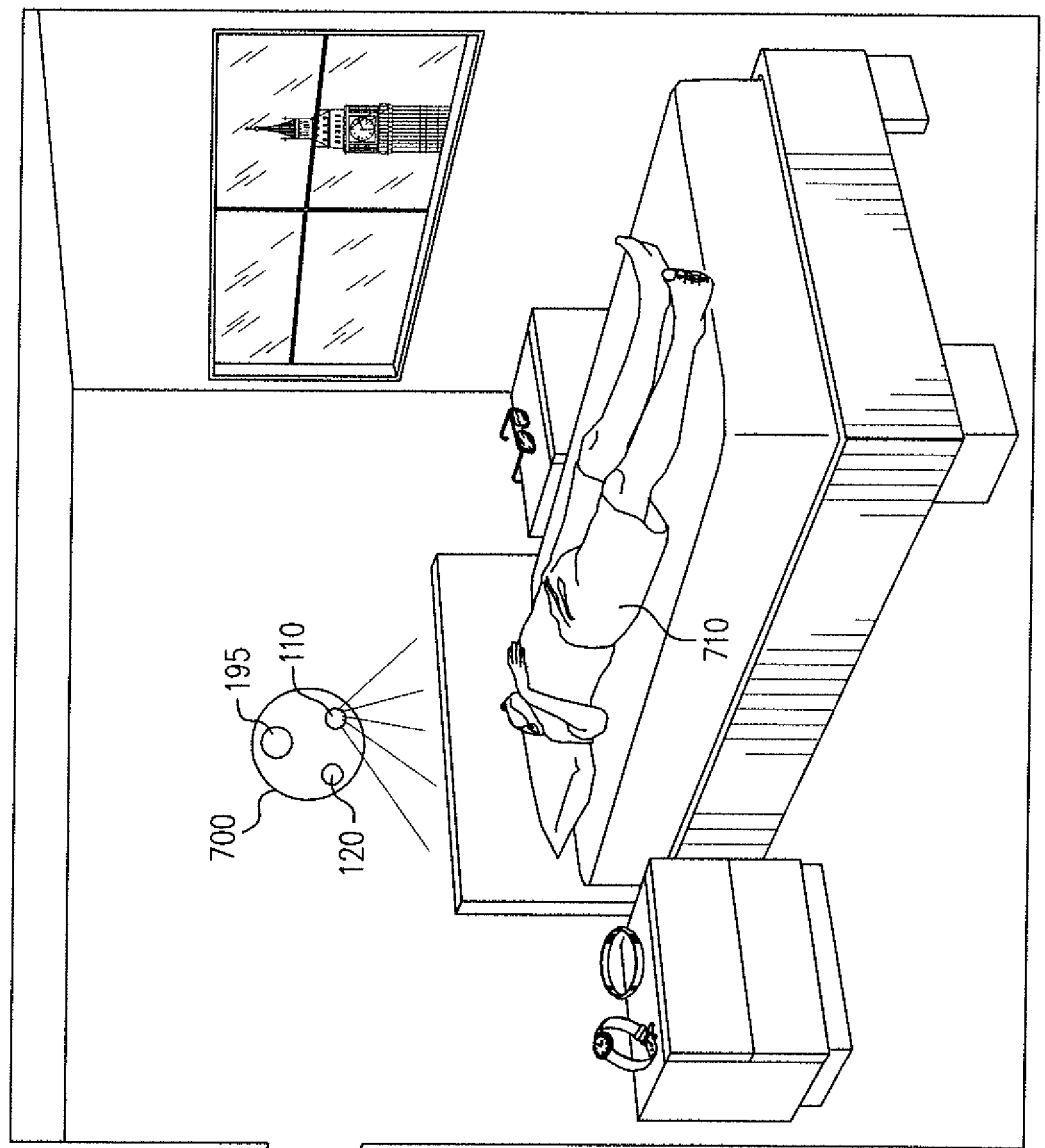
FIG. 7A is a schematic illustration of a personal alarm system, according to an exemplary embodiment of the disclosure.
Figure 7A:
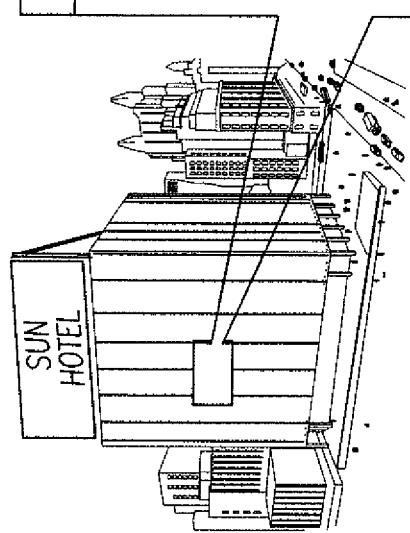
Figure 7B:
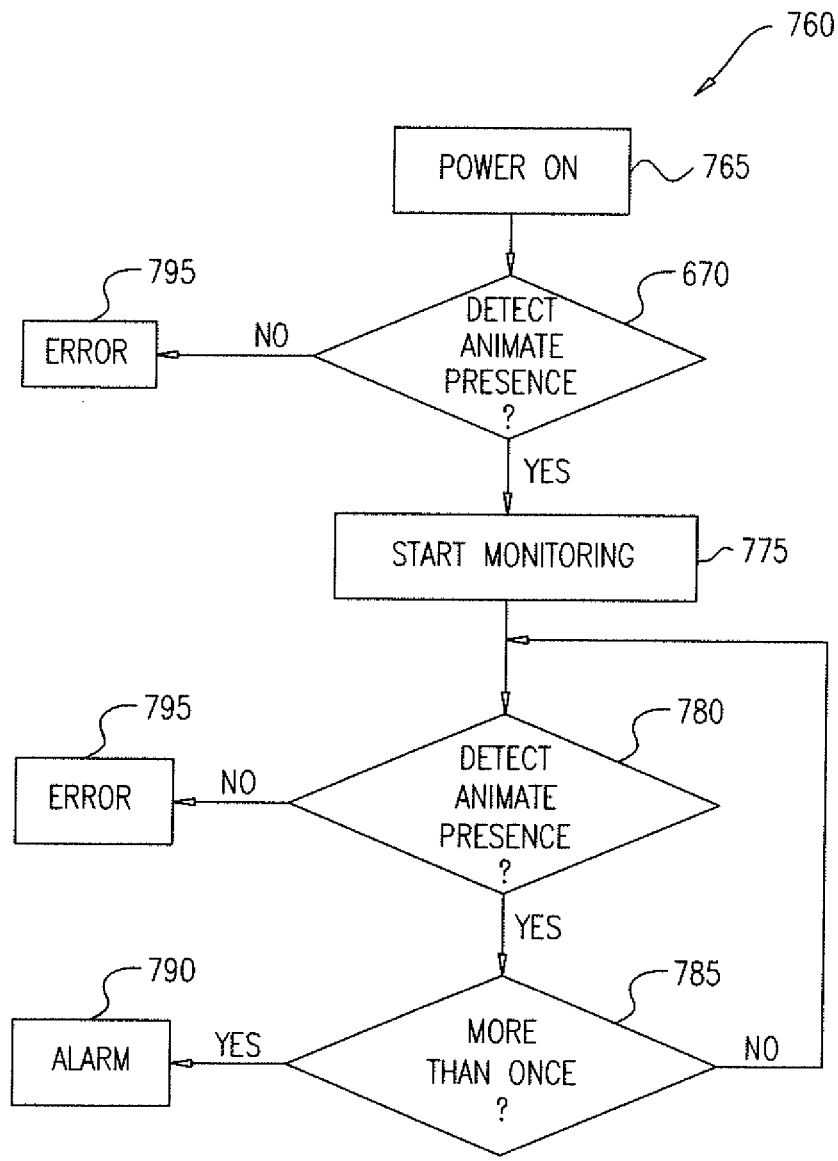
FIG. 7B is a flow diagram of a personal alarm system, according to an exemplary embodiment of the disclosure.

FIG. 7A is a schematic illustration of a personal alarm system 700 and FIG. 7B is a flow diagram 760 of personal alarm system 700, according to an exemplary embodiment of the disclosure. The personal alarm system can be used in a room in which a person 710 is situated alone and warn the person 710 if someone else enters the room, for example when the person 710 is asleep in a hotel room the person can be protected from thieves while sleeping. In some embodiments of the disclosure, personal alarm system 700 can be used to protect more than one person, for example 2, 3 or 4 people. In an exemplary embodiment of the disclosure, personal alarm system 700 may be placed at one side of the room to monitor the room with one or more ultrasonic transducers 110 and one or more ultrasonic receivers 120. Optionally, the transducers 110 and receivers 120 are configured to cover 120 to 180 degrees around personal alarm system 700 to cover all of the room or at least covering the person and entrances to the room.

In an exemplary embodiment of the disclosure, the user powers on 765 the personal alarm system 700 for it to start monitoring. Personal alarm system 700 begins by detecting animate presence 770 (the person 710) and providing an indication (e.g. a LED) that it is functioning. The personal alarm system 700 starts monitoring the room 775. While monitoring the personal alarm system 700 detects animate presence 780 and then determines if it detected a single person or more 785. If only a single person was detected the personal alarm system continues to monitor the room. Otherwise if no animate presence is detected the personal alarm system provides an error indication 795. Likewise if personal alarm system 700 detects more than one person it activates an alarm 790 to warn the person or other people (e.g. body guards that are located in another room). Optionally, personal alarm system 700 includes communication unit 195 that calls or sends a message to the other people and/or personal alarm system 700 may provide an indication in the form of an audible tone to wake up the person 710, scare an intruder or summons help.

Figure 8A:
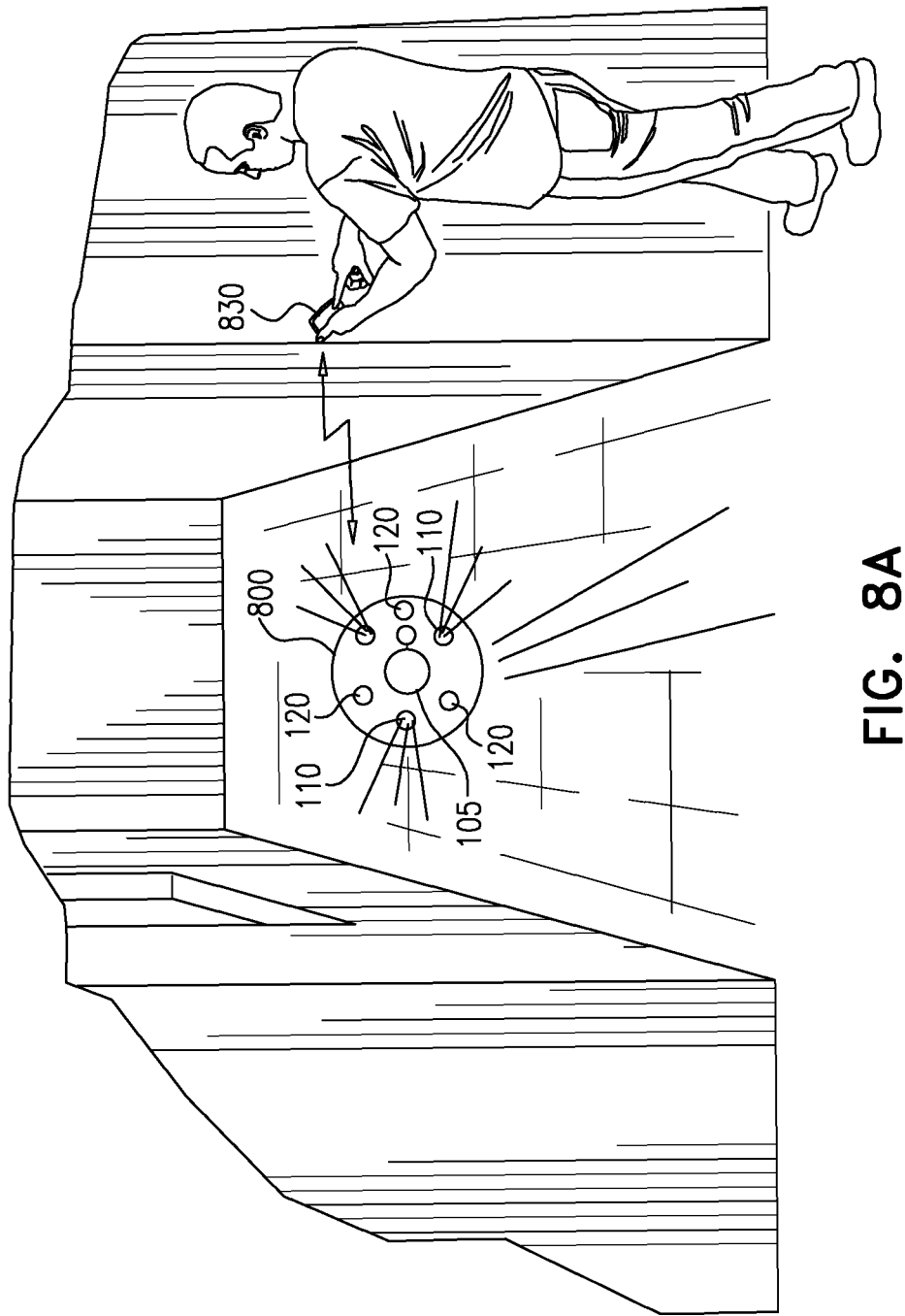
FIG. 8A is a schematic illustration of a preview security system, according to an exemplary embodiment of the disclosure.
Figure 8B:
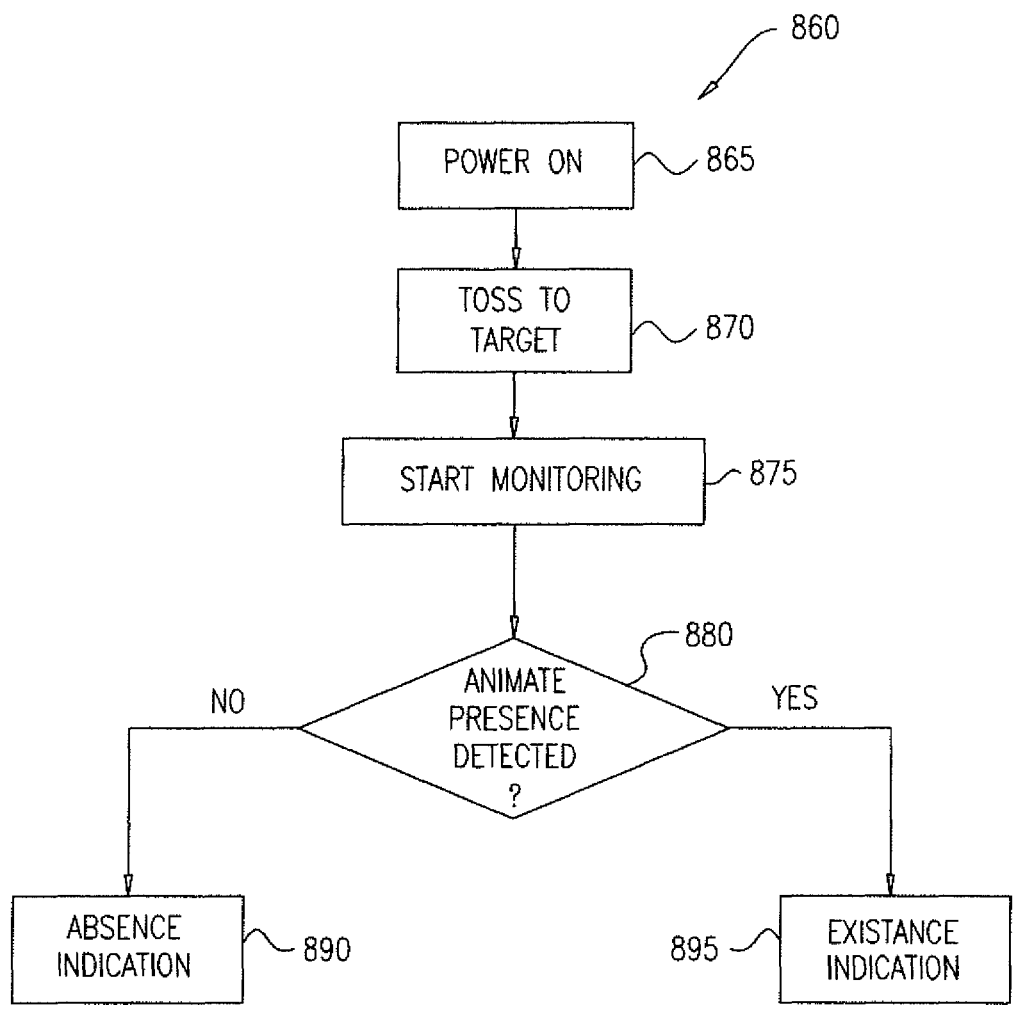
FIG. 8B is a flow diagram of a preview security system, according to an exemplary embodiment of the disclosure.

FIG. 8A is a schematic illustration of a preview security system 800, and FIG. 8B is a flow diagram 860 of preview security system 800, according to an exemplary embodiment of the disclosure. In many cases it is desirable to be able to know if there are people or animals around the corner or in a room without actually going there. In an exemplary embodiment of the disclosure, preview security system is designed as a ball that can be tossed into the room, around the corner or into a cave or other places to check if there is animate presence before entering. Optionally, preview security system includes ultrasonic transducers 110 and ultrasonic receivers 120 at various locations on the surface of the ball, so that preview security system 800 can monitor in substantially any direction. In an exemplary embodiment of the disclosure, the preview security system includes electronic circuit 105 for analyzing the measurements of the ultrasonic transducers 110 and ultrasonic receivers 120. The results of the analysis are then transmitted wirelessly via communication unit 195 to a remote receiver 830. Optionally, the communications may be transmitted using an RF signal or other types of wireless communications.

In an exemplary embodiment of the disclosure, preview security system 800 is powered on 865 by the user. Then it is tossed 870 into the room (e.g. through a window), into a cave, over a fence, around a wall or into any place that is of interest to check. Optionally, preview security system 800 starts monitoring 875 by measuring and analyzing the measurements to determine if there is animate presence 880 in the vicinity of the preview security system 800. Optionally the preview security system 800 then transmits wirelessly to remote device 830 an indication if it detected the existence of animate presence 895 or the absence of animate presence 890 so that the user may respond accordingly.

It should further be appreciated that the above described methods and apparatus may be varied in many ways, including omitting or adding steps, changing the order of steps and the type of devices used. It should be appreciated that different features may be combined in different ways. In particular, not all the features shown above in a particular embodiment are necessary in every embodiment of the disclosure. Further combinations of the above features are also considered to be within the scope of some embodiments of the disclosure. It will also be appreciated by persons skilled in the art that the present disclosure is not limited to what has been particularly shown and described hereinabove.

I claim:

1. A system for monitoring animate presence, comprising:
   one or more ultrasonic transducers configured to transmit an ultrasonic signal comprising a train of pulses;
   one or more ultrasonic receivers configured to receive an echo signal in response to the transmitted ultrasonic signal, the echo signal comprising multiple pulses in response to the train of pulses of the transmitted signal;
   an electronic circuit for comparing the transmitted signal to the received echo signal to identify a phase shift between the transmitted signal and the received echo signal, and additionally depicting the multiple pulses of the received echo signal to overlap in a graph to view positions in which the multiple pulses differ and transforming the multiple pulses to a frequency domain graph to detect frequencies of breathing and heartbeats caused by animate presence; wherein the electronic circuit identifies animate presence based on the identified phase shift and the depicted graphs.

2. The system according to claim 1, wherein the electronic circuit is configured to differentiate between a single animate entity and multiple animate entities.

3. The system according to claim 1, wherein the electronic circuit is configured to differentiate between people and animals.

4. The system according to claim 1, wherein the electronic circuit is configured to send notification if more than one person is detected in a monitored room.

5. The system according to claim 1, wherein the electronic circuit is configured to monitor a Wi-Fi connection and provide a notification if the Wi-Fi connection is unavailable and there exists animate presence.

6. The system according to claim 1, wherein the electronic circuit is configured to monitor the respiratory activity of an observed individual and activate an alarm if the respiratory activity ceases or is abnormal.

7. The system according to claim 1, wherein the electronic circuit is configured to monitor animate presence in a closed area and activate an alarm if no animate presence is detected or more than one organism is detected.

8. The system according to claim 1, wherein the system includes a communication unit for providing results with a wireless electromagnetic signal.

9. The system according to claim 1, wherein the system is configured to monitor animate presence in a room and provide the results to a user in a different room.

10. The system according to claim 1, wherein the system is shaped as a sphere with multiple ultrasonic transducers aimed in different directions to monitor in substantially any direction.

11. A method of monitoring animate presence, comprising:
    transmitting an ultrasonic signal comprising a train of pulses using one or more ultrasonic transducers;
    receiving an echo signal comprising multiple pulses in response to the transmitted ultrasonic signal by one or more ultrasonic receivers;
    comparing the transmitted signal to the received echo signal using an electronic circuit to identify a phase shift between the transmitted signal and the received echo signal, and additionally depicting the multiple pulses of the received echo signal to overlap in a graph to view positions in which the multiple pulses differ and transforming the multiple pulses to a frequency domain graph to detect frequencies of breathing and heartbeats caused by animate presence; and
    identifying animate presence based on the identified phase shift and the depicted graphs.

12. The method according to claim 11, wherein the electronic circuit is configured to differentiate between a single animate entity and multiple animate entities.

13. The method according to claim 11, wherein the electronic circuit is configured to differentiate between people and animals.

14. The method according to claim 11, wherein the electronic circuit is configured to send notification if more than one person is detected in a monitored room.

15. The method according to claim 11, wherein the electronic circuit is configured to monitor a Wi-Fi connection and provide a notification if the Wi-Fi connection is unavailable and there exists animate presence.

16. The method according to claim 11, wherein the electronic circuit is configured to monitor the respiratory activity of an observed individual and activate an alarm if the respiratory activity ceases or is abnormal.

17. The method according to claim 11, wherein the electronic circuit is configured to monitor animate presence in a closed area and activate an alarm if no animate presence is detected or more than one organism is detected.

18. The method according to claim 11, wherein results of the identifying are provided by a wireless electromagnetic signal.

19. The method according to claim 11, wherein the monitoring is performed in a room and results are provided to a user in a different room.

20. The method according to claim 11, wherein the system is shaped as a sphere with multiple ultrasonic transducers aimed in different directions to monitor in substantially any direction.

* * * * *